United States Patent [19]

Mockapetris et al.

[11] Patent Number: 5,606,515
[45] Date of Patent: Feb. 25, 1997

[54] SENSOR CONDITIONING CIRCUITRY FOR USE WITH ELECTRICALLY EXCITED TRANSDUCERS

[75] Inventors: Robert F. Mockapetris, Weymouth; Fred L. Lehman, Sharon, both of Mass.

[73] Assignee: Instron Corporation, Canton, Mass.

[21] Appl. No.: 13,066

[22] Filed: Feb. 3, 1993

[51] Int. Cl.$^6$ ............................... G01B 7/16; G01L 1/26
[52] U.S. Cl. ................... 364/571.04; 324/207.16; 364/481; 364/506
[58] Field of Search .................... 364/508, 480, 364/481, 550, 560, 571.01, 571.04, 571.07, 505, 506; 324/207.16, 207.18, 209; 340/870.35, 870.36

[56] References Cited

U.S. PATENT DOCUMENTS

| | | |
|---|---|---|
| 4,599,560 | 7/1986 | Sanford et al. ............... 324/207.18 |
| 4,724,419 | 2/1988 | Kreuzer . | |

FOREIGN PATENT DOCUMENTS

| | | |
|---|---|---|
| 2219659 | 12/1989 | United Kingdom . |
| 2241330 | 8/1991 | United Kingdom . |

OTHER PUBLICATIONS

Electronic Components and Circuits, Hardware Techniques and Processes, NASA Tech Briefs, Mar. 1992.

Chrysafis, A., "Digital Sine–Wave Synthesis Using the DSP56001", Motorola, Apr. 1, 1988.

Rader, C. M., "Method and Apparatus for Sampling In–Phase and Quadrature Components", The MIT Report, Oct. 1991.

Kehrer, R., "MGC Measuring Amplifier System—the optimum combination of analog and digital technologies drastically changes current amplifier structures", paper distributed publicly in 1990.

McCune, E., "Create signals having optimum resolution, response and noise", Digital RF Solutions Corp., EDN, pp. 95–107, Mar. 14, 1991.

Koljonen, T. et al., "Averaging increases μP's ADC resolution", Design Ideas EDN, pp. 139–140, Feb. 1, 1990.

*Primary Examiner*—Edward R. Cosimano
*Assistant Examiner*—Edward Pipala

[57] ABSTRACT

Circuitry that is used to determine the strain of a component and includes a waveform random access memory that stores excitation digital data that represent values of an excitation waveform, a digital-to-analog converter to convert the digital data to an analog excitation signal, a strain sensing transducer that receives the excitation signal and generates an analog response signal, an analog-to-digital converter that digitizes the transducer response signal, a demodulator that multiplies the digital response signal times phase adjusted values of the excitation digital data stored in the waveform memory and low-pass filters the digital response signal, and a resistance-to-voltage converter connected to present a voltage indicating the resistance of an identifying resistor to the analog-to-digital converter. Also disclosed are the use of a serial data transmission line to transmit multiplexed excitation waveform data from a host to a plurality of slave sensor conditioning boards and a calibration technique for calculating a phase shift angle for the demodulator.

41 Claims, 7 Drawing Sheets

SENSOR CONDITIONING CIRCUITRY FOR USE WITH ELECTRICALLY EXCITED TRANSDUCERS

BACKGROUND OF THE INVENTION

The invention relates to circuits for providing alternating current excitation waveforms for transducers used in material testing and other applications.

Alternating current (AC) excitation has been employed with electronic transducers such as strain gauges to reduce noise (which typically is higher at lower frequencies and can be cancelled out) and drift (which typically is direct current). Some transducers, such as LVDTs, require AC excitation.

In material testing load frames used to measure stress and strain of samples, AC excitation has typically been implemented by analog oscillators with analog components. Analog components have also typically been used for demodulation of the transducer's signal, for filtering, and for ranging, a technique used to obtain better accuracy and dynamic range. Potentiometers were used for circuit alignment.

SUMMARY OF THE INVENTION

In one aspect, the invention features, in general, circuitry that is used to determine the strain of a component and includes a random access waveform memory to store digital data representing values of an excitation waveform that are converted at a digital-to-analog converter to an analog excitation waveform signal that is applied to a strain sensing transducer. With this approach one can easily change the frequency, amplitude, and waveform shape by simply changing the digital data that are stored.

In preferred embodiments the waveform memory stores excitation waveforms for a plurality of digital-to-analog converters and associated strain sensing transducers. The waveforms for different transducers can have different frequencies, different amplitudes and different shapes.

In another aspect, the invention features, in general, circuitry that is used to determine the strain of a component and includes a waveform memory that stores excitation digital data that represent values of an excitation waveform, a digital-to-analog converter to convert the digital data to an analog excitation signal, a strain sensing transducer that receives the excitation signal and generates an analog response signal, an analog-to-digital converter that digitizes the transducer response signal, and a digital demodulator that demodulates the digital response signal based on the excitation digital data stored in the waveform memory. This technique provides simple and accurate demodulation of the digital response.

In preferred embodiments the excitation digital data used at the demodulator are phase shifted to be in phase with the digital response signal. This phase correction acts to reject quadrature components (which can cause parasitic effects such as sensitivity to cable movement) and tends to give the electrical signal more "headroom" (e.g., avoid problems resulting from the in-phase demodulated component being much smaller than the out-of-phase component of a severely phase-shifted signal). When a linear variable differential transformer is used as the transducer, this phase correction causes rejection of the phase component which contains the resistance of the transformer winding in its transfer function. The phase correction is preferably implemented by adjusting the values of the excitation digital data to have values of the waveform shifted by the phase shift angle, permitting very accurate angular correction. Preferably the circuitry also includes an adder that is used to add an imbalance correction value to the digital data output by the demodulator and a span correction multiplier that multiplies a span correction factor times the digital data output by the adder. Preferably the demodulator includes a multiplier that multiplies the phase shifted excitation values and a digital low-pass filter that filters the digital response signal to remove alternating current components in the digital response. The analog-to-digital converter has a sample rate that is sufficiently high to allow noise bandwidths sufficient to exercise the converter through plural codes. The low-pass filter is implemented by a processor that does the averaging of the digital filtering with higher resolution than that of the converter, providing measurements having resolution that is better than that of the converter. The bandwidth of the analog response signal is much larger than the bandwidth of the digital low-pass filter. The digital low-pass filter has an output with a lower rate than the sample rate of the analog-to-digital converter. The analog-to-digital converter outputs data no more than 16 bits wide, and the processor operates on 32-bit floating point data. The digital low pass filter is a multiple-stage, multirate filter. There also is an analog anti-aliasing low-pass filter having a cutoff frequency at ½ the sample rate of the analog-to-digital converter.

In another aspect, the invention features, in general, circuitry that is used to determine the strain of a component and includes a waveform generator outputting an analog excitation waveform signal, a strain sensing transducer that receives the excitation signal and generates an analog response signal, an analog-to-digital converter outputting digital data words with a bit width of 16-bits or greater, a resistance-to-voltage converter that has a voltage output that is a function of the resistance of an identification resistor mounted on the transducer, and a switch that connects either the transducer response signal or the identification resistor voltage output to the analog-to-digital converter. The resistance-to-voltage converter includes a low offset operational amplifier stage and a reference resistor with 0.1% accuracy. This permits the same high-accuracy components used to do the strain measurements to also be used to accurately measure the identifying resistance. Also, the resistance-to-voltage converter and the analog-to-digital converter have the same reference voltage, also promoting accuracy.

In another aspect, the invention features, in general, circuitry that generates waveforms for multiple channels and includes a host digital waveform circuit and a plurality of slave waveform circuits connected to the host waveform circuit by a common serial data transmit line. The host waveform circuit serially outputs a multiplexed series of digital data words representing a plurality of excitation waveforms and channel information identifying the channels to which the individual digital data words relate. Each slave waveform circuit includes a channel discriminator, a latch, and a digital-to-analog converter. The channel discriminator determines from the channel information whether a particular digital data word is intended for that slave waveform circuit and controls the latch to latch digital data words intended for that slave waveform circuit. This permits efficient use of the host waveform circuit circuitry for a plurality of channels and efficient transmission of digital data to all channels over a single line.

In preferred embodiments the channel discriminator includes a state machine implemented on a programmable logic device. The channel information used to identify channels are channel codes that are unique for each slave circuit, and each channel discriminator has inputs identifying its unique channel code. The digital data words are transmitted with associated channel codes in frames, and the host waveform circuit generates a frame synchronization signal distributed to the slave waveform circuits over a frame synchronization line. The host waveform circuit also generates a clock signal distributed to the slave waveform circuits over a clock line. The slave waveform circuit includes an input shift register into which all of the digital data words for all channels are shifted, and the latch is controlled by a load pulse from the channel discriminator to present only the digital data words intended for that channel to the digital-to-analog converter.

The host waveform circuit also preferably receives response data from all slave waveform circuits. The slave circuits include analog-to-digital converters, and response digital data words are transmitted over the data receive line in time slots determined by the channel discriminators. The same unique channel codes used to identify excitation digital data words intended for a channel are used to identify the time slots for the response data words. The frame synchronization pulses are used to define time slots, and the clock pulses are used at an output shift register to shift bits of the response digital data words onto the data receive line.

In another aspect, the invention features, in general, a method of measuring using excitation waveforms that includes the steps of reading digital data from a waveform memory to provide a digital excitation waveform signal, converting the digital excitation waveform signal at a digital-to-analog converter to an analog excitation waveform signal, sensing a physical phenomenon with a transducer that receives the analog excitation waveform signal and outputs an analog response signal, digitizing the analog response, determining a phase angle between the digitized response signal and the digital excitation waveform signal, phase shifting the excitation digital data by the phase angle to provide phase-shifted excitation digital data that are in phase with the digital response signal, and demodulating the digital response signal based on the phase-shifted excitation digital data at a demodulator to obtain a demodulated digital output.

In preferred embodiments the phase angle is determined during a calibration procedure by taking measurements with different phase angles between the excitation digital data applied to the demodulator and the response signal. In particular, measurements are made at different phenomenon conditions without any phase shifting of the excitation digital data applied to the demodulator to obtain a real part and measurements are also taken for the same phenomenon conditions with 90° phase shifting of the excitation digital data applied to the demodulator to obtain an imaginary part. The difference between the imaginary parts and real parts results in a calibration vector, the angle of which is taken as the phase angle between the digital response signal and the digital excitation waveform signal. The preferred use of the method is in a material testing load frame, and the two phenomenon conditions used for calibration are the zero point and a span calibration point provided by a known load or, e.g., a shunt resistor. The magnitude of the calibration vector can be used to adjust the amplitude of the excitation digital data prior to converting at the digital-to-analog converter. The calibration procedure can also include calculation of an imbalance correction factor and a span correction factor after the phase angle has been calculated. Measurements are taken (with the excitation digital data being phase shifted by the phase angle before applying to the demodulator) at different known phenomenon conditions; the imbalance correction value is based upon the difference between the expected and the measured lower phenomenon condition, and the span correction value is based upon the ratio of the measured difference between values and the expected difference. The imbalance correction value is added to the demodulated digital output, and the span correction value is multiplied times the imbalance-corrected value.

Other advantages and features of the invention will be apparent from the following description of the preferred embodiment thereof and from the claims.

DESCRIPTION OF THE PREFERRED EMBODIMENT

The drawings will be described first.

Drawings FIG. 1 is a block diagram showing circuitry used with a material testing instrument according to the invention.

Structure

Figure 1:
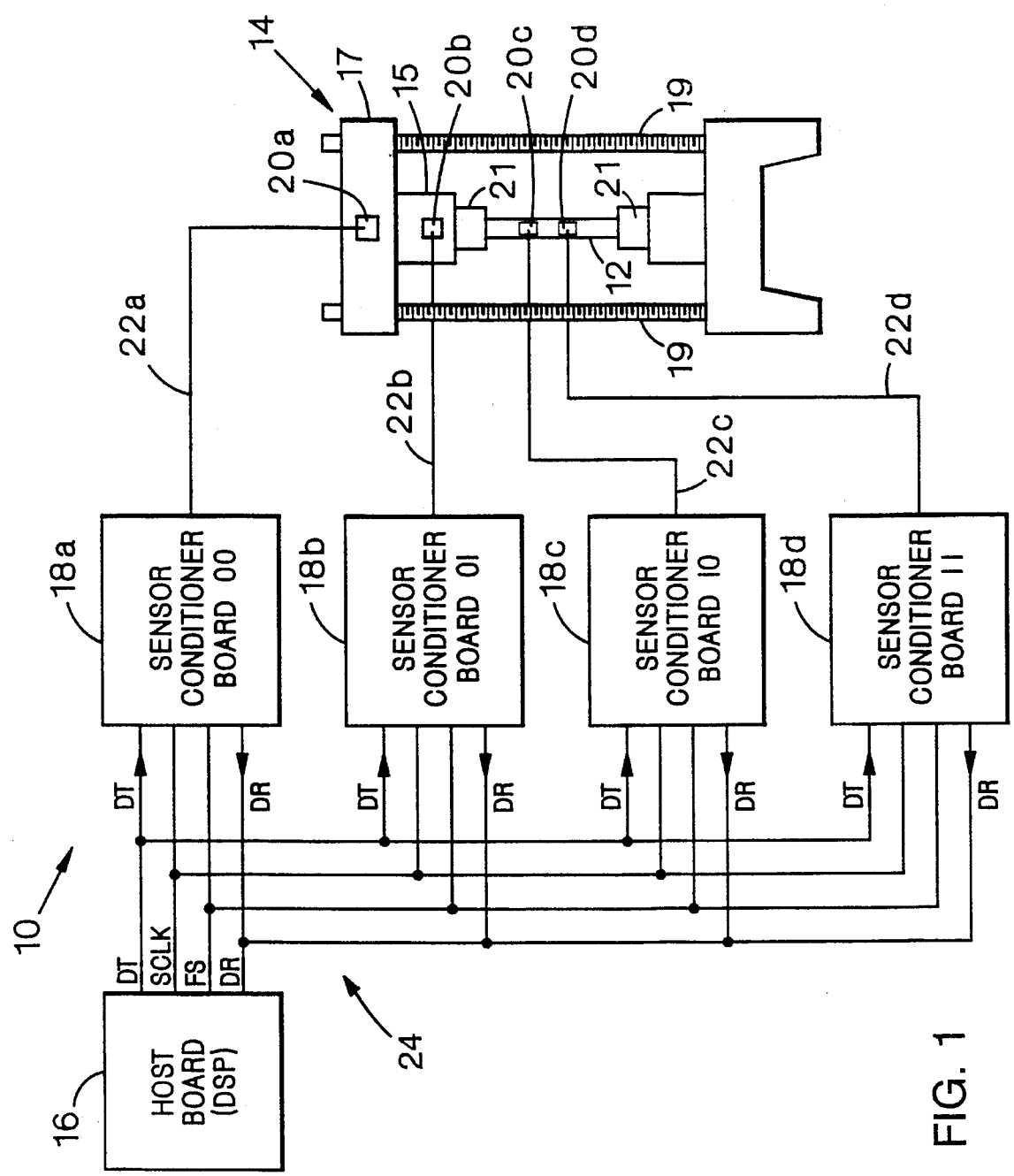

Referring to FIG. 1, there is shown system 10 for determining strains on sample 12 on material testing load frame 14. The load string of load frame 14 includes cross-head 17, driven by lead screws 19 (in turn driven by a DC motor, not shown), load cell 15, grips 21, and sample 12. A servo hydraulic actuator could be used in place of lead screws 19. System 10 also determines the load being applied at load cell 15 and displacement of cross-head 17 of load frame 14. The circuitry of system 10 includes a host board 16 and four sensor conditioning boards 18a–18d associated with respective transducers 20a–20b, transducer 20a being mounted on cross-head 17, transducer 20b being mounted on load cell 15, and transducers 20c and 20d being mounted at different orientations and positions on sample 12. Sensor conditioning boards 18a–18d act as slaves that are controlled by host board 16. Host board 16 communicates with all sensor conditioning boards 18a–18d via four serial lines 24 that provide respective DT, SCLK, FS, and DR signals. Excitation waveforms are transmitted in digital form over the line 24 designated DT, and response signals are transmitted over the line 24 designated DR. Lines FS and SCLK are used for synchronization. Sensors 20a–20d are connected to boards 18a–18d via respective lines 22a–22d.

Figure 2:
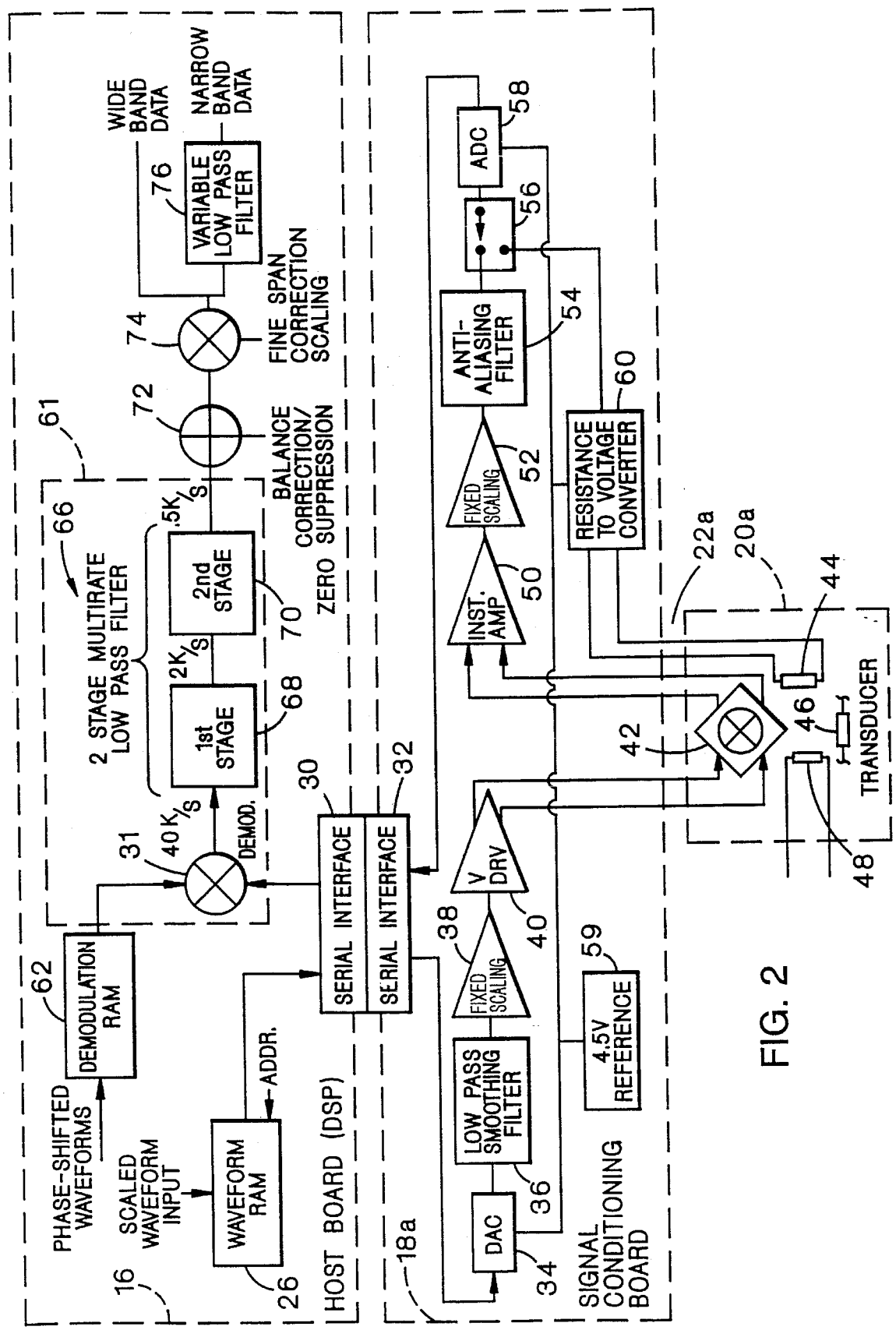
FIG. 2 is a functional block diagram of components of the FIG. 1 circuitry.

FIG. 2 shows the digital signal processing components and functions of host board 16 and the digital and analog circuit components of sensor conditioning board 18a (boards 18b–18d are identical). FIG. 3 shows the components in host board 16 and sensor conditioning board 18a providing a multiplexed serial interface between host board 16 and sensor conditioning boards 18a. Host board 16 is based on a 32-bit floating point digital signal processor (DSP) available from Texas Instruments under the TMS 320C31 trade designation. It includes random access memory available for data and program, an arithmetic logic unit, and high-speed buffers to provide the memories, processing and buffering shown on FIGS. 2 and 3.

Referring to FIG. 2, waveform RAM 26 stores digital data representing values of the four excitation waveforms to be applied to respective transducers 20a–20d. The amplitudes of the waveforms in waveform RAM 26 are preset as part of the calibration procedure. The digital signal processor on board 16 includes an address generator to repetitively address waveform RAM 26 to repetitively read out the digital data representing the excitation waveforms. The output of waveform RAM 26 passes through serial interface 30 on board 16 and serial interface 32 on boards 18a–18d (both shown in more detail on FIG. 3).

In board 18a, shown in detail on FIG. 2, the digital data output of serial interface 32 is connected to serial digital-to-analog converter (DAC) 34, a 12-bit, two's complement serial input, bipolar voltage output DAC with a 40 ks/s data transfer rate. The output of serial DAC 34 is connected to low-pass smoothing filter 36, which is a two-pole low-pass Butterworth filter employing stable silver mica capacitors to assure phase stability. The output of filter 36 is connected to fixed scaling amplifier 38, the output of which is connected to voltage driver 40, a push-pull balanced voltage driver. The output of voltage driver 40 is provided over wires 22a to strain gauge resistance bridge 42 of transducer 20a. In wires 22a, the excitation lines are shielded separately from the response lines. Transducer 20a also includes identification resistor 44 and shunt resistor 46. Identification resistor 44 has a precise coded resistance to identify the class and units of transducer 20a. Shunt resistor 46 is activated by electrical calibration relay drive 48 to provide a known resistance for calibration purposes for transducer 20a.

The output of bridge 42 is connected to instrumentation amplifier 50, which converts the balanced, low-level differential output from bridge 42 to an amplified, single-ended output signal. Amplifier 50 is implemented using a classical three operational amplifier configuration using amplifiers with a maximum input noise density of 4 nv/rt(Hz). The gain of 21 of the first stage is implemented with a 10K/1K/10K resistor network. These values have been selected to guarantee the minimum noise needed to exercise analog-to-digital converter (ADC) 58 through plural codes in order to get enhanced accuracy through digital filtering.

Fixed scaling 52 provides a gain of 7.4 to the output of instrumentation amplifier 50 before passing the signal to anti-aliasing filter 54, which has a cut-off frequency of 20 kHz, ½ the sample rate of ADC 58. In general, the cut-off frequency should be as high as possible up to ½ the sample rate of ADC 58: if it is higher than ½, noise will be increased: if it is reduced significantly below ½, the enhancement of resolution obtained by oversampling will be reduced.

Figure 5:
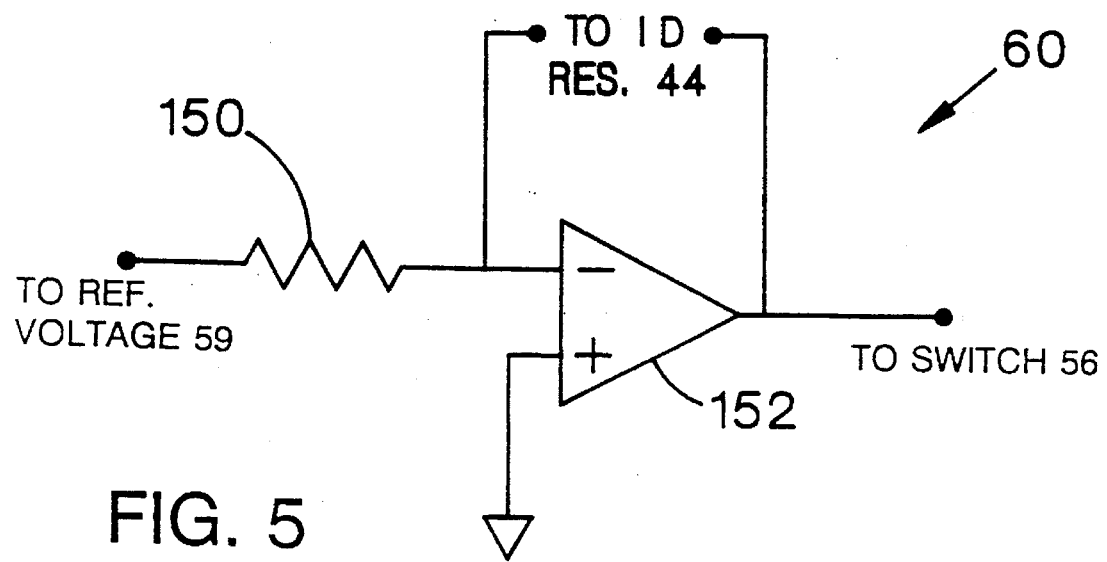
FIG. 5 is a diagram of a resistance-to-voltage converter on a FIG. 1 slave sensor conditioning board.

Switch 56 is a field effect transistor switch which allows connection to resistance-to-voltage converter 60 during the calibration procedure. Resistance-to-voltage converter 60 is driven from the same DC reference as ADC 58 and DAC 34, namely DC reference 59. Referring to FIG. 5, resistance-to-voltage converter 60 includes precision reference resistor 150 (0.1% accuracy) and low-offset operational amplifier 152 (e.g., OP07 from Analog Devices), having an offset less than 1 mv. Switch 56 permits measurement of the resistance of identifying resistor 44 using the same high-accuracy components used to process measurements from strain gauge bridge 42.

Serial ADC 58 is a high-performance, bipolar voltage input, two's complement serial output, 16-bit ADC with an integral nonlinearity error (INL) of 1 least significant bit (lsb) and a differential nonlinearity (DNL) error of ½ lsb. A suitable ADC is available from Crystal Semiconductor under the 5101 trade designation. ADC 58 is monotonic and has an offset error that does not exceed 5 lsbs and full scale error that does not exceed 5 lsbs. The digital output of ADC 58 is connected to serial interface 32, in turn connected to serial interface 30 on board 16. Serial interface 30 is connected to demodulator 61, including demodulating multiplier 31 and digital low-pass filter 66. Demodulating multiplier 31 multiplies the response signal from serial interface 30 by the excitation waveform values that have been corrected for phase angle and stored in demodulation RAM 62. The output of demodulating multiplier 31 is connected to two-stage multirate, low-pass filter 66, including first stage 68 and second stage 70. First stage 68 is implemented as a finite impulse response filter with a transition band that starts at 100 Hz and ends at 1750 Hz at 40 db down. The output of first stage 68 is decimated from 40,000 samples/sec. (s/s) to 2,000 s/s. Second stage 70 of filter 66 is a four-pole, elliptic design with a transition band running from 100 Hz to 250 Hz. The overall effect of the two cascaded stages is a low-pass filter with a bandwidth of 100 Hz and a stop band beginning at 250 Hz at 40 db down. The output of second stage 70 is further decimated by a factor of four, yielding 500 samples/second. The output of filter 66 is connected to adder 72, for correction for transducer imbalance errors. The output of adder 72 is connected to multiplier 74, for correction for span errors. The output from multiplier 74 is connected to variable low-pass filter 76.

Figure 3A:
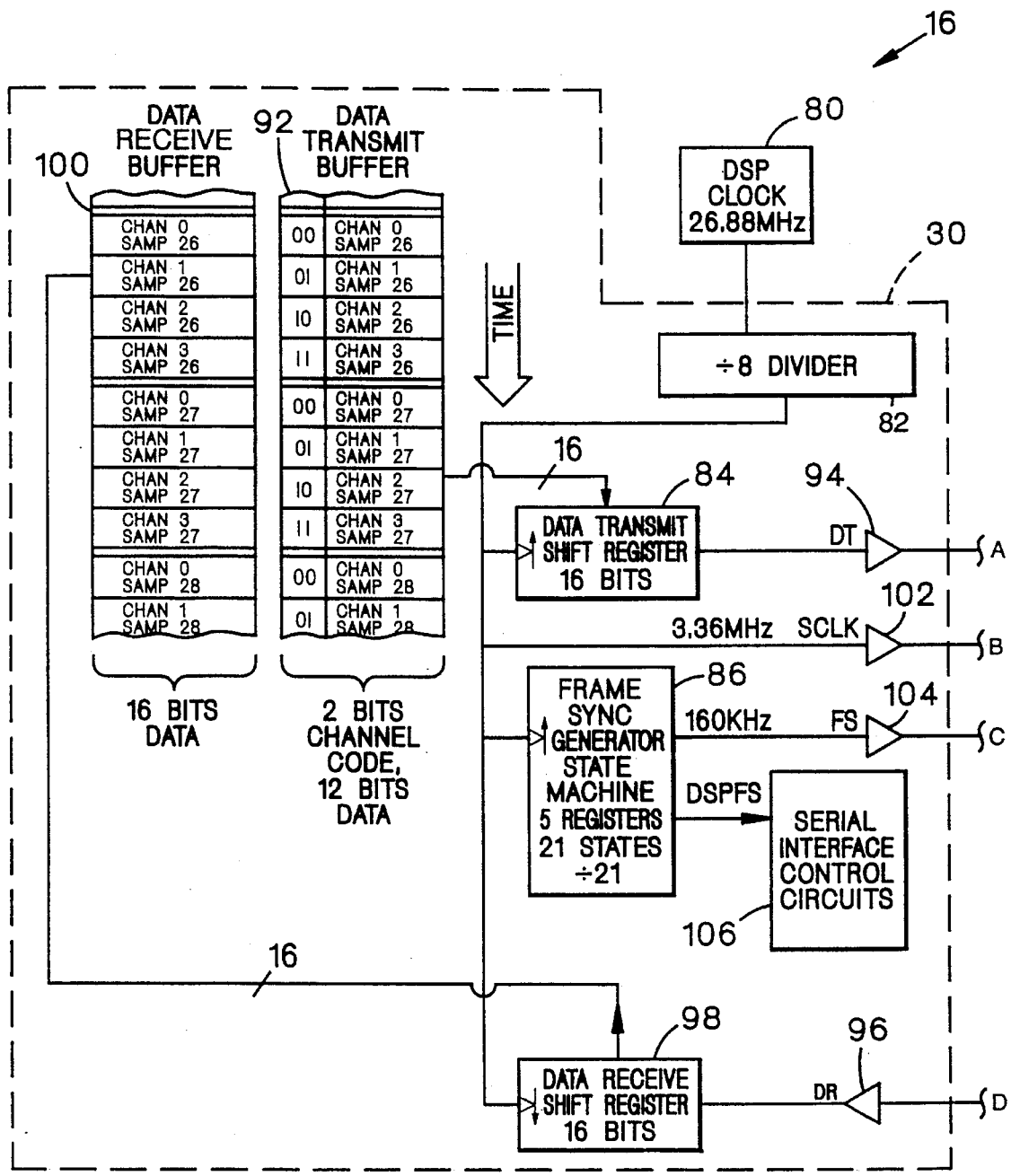
FIG. 3A and 3B is a block diagram showing the components on a host board and on one of the slave sensor conditioning boards of the FIG. 1 circuitry that provide a serial interface between the two.
Figure 3B:
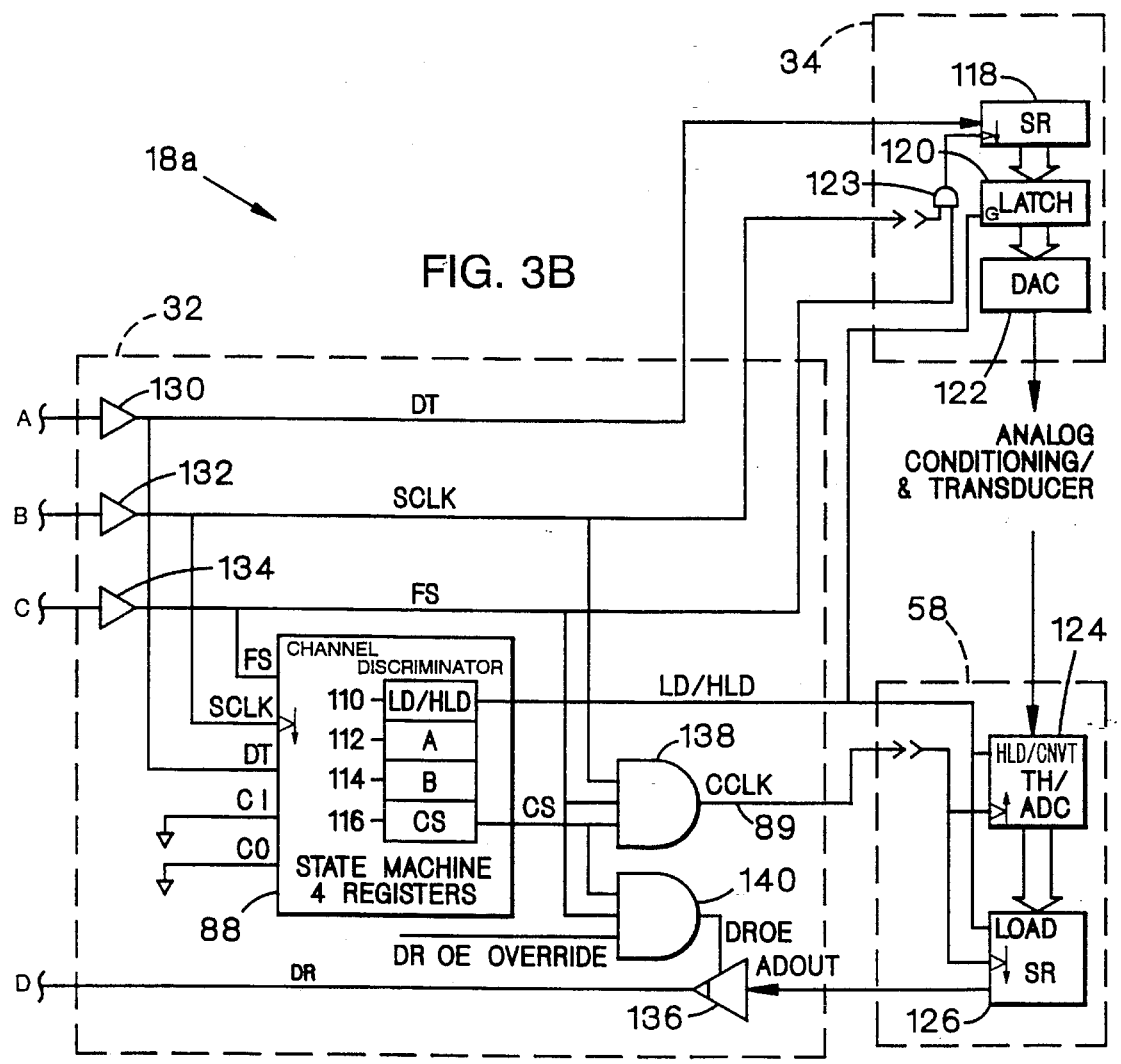

Referring to FIGS. 3A and 3B a four-channel serial interface is provided by serial interface 30 in host board 16 and serial interface 32 in the four sensor conditioning boards 18a–18d. (Only board 18a is shown on FIG. 3.) DSP clock 80 in the DSP in host board 16 has a 26.88 MHz frequency that is divided to provide the frequencies employed by serial interfaces 30, 32. All of the components shown on FIG. 3 for host board 16 are internal to the DSP with the exception of frame synchronization generator 86. Data transmit buffer 92 stores the 12-bit excitation waveform values from multiplier 28 (FIG. 2) in interleaved order along with associated 2-bit channel codes. Sixteen-bit data transmit shift register 84 is connected to receive digital data words stored in buffer 92 and output the words one bit at a time to buffer 94, which buffers the data provided to the DT line. Data receive shift register 98 is similarly connected to receive response data one bit at a time from buffer 96 and output 16-bit words to data receive buffer 100, in which the words are stored in interleaved order for the four channels and ready for access by demodulating multiplier 31 (FIG. 2). The sample clock (SCLK) and the frame synchronization (FS) lines have respective buffers 102 and 104 on host board 16. Frame synchronization generator 86 includes a state machine with five registers and 21 states. Also included on board 16 is serial interface control circuit 106.

Serial interface 32 includes channel discriminator 88, input buffers 130, 132, 134, output buffer 136, and output gates 138, 140. (Inversions are not shown on FIGS. 3A and 3B.) Channel discriminator 88 is an 8-output, 25 ns, programmable logic device (PLD). It receives the FS, SCLK and DT signals from host board 16 along with ground reference voltages at C1 and C0 to provide the "00" channel code identifying board 18a as Channel 0. Boards 18b, 18c, and 18d have C1, C0 CMOS inputs of 0 V, 5 V; 5 V, 0 V; and 5 V, 5 V to provide 01, 10, and 11 codes identifying these boards as channels 1, 2, and 3, respectively. The PLD is configured as a state machine with four registers 110, 112, 114, 116 and is configured to generate the load/hold (LD/HLD) and channel select (CS) signals as indicated on FIG. 4. Registers 110 and 116 are used to generate the LD/HLD and CS outputs, respectively: registers 112, 114 are internal registers. Serial input DAC 34 includes 16-bit input shift register 118, latch 120, parallel DAC 122, and gate 123. Serial output ADC includes parallel output DAC 124 (a track and hold converter) and 16-bit output shift register 126.

Operation

In operation, individual, respective excitation waveforms are generated for each transducer 20a–20d at host board 16 in digital form and are provided over the line 24 designated DT to sensor conditioning boards 18a–18d for conversion at the respective board 18a–18d to analog form and application to respective strain gauges 20a–20d over lines 22a–22d. The sensed signals (which are functions of both excitation signals and the sensed strains) are converted to digital form by sensor conditioning boards 18a–18d and provided over the line 24 designated DR to host board 16 for processing.

Prior to measurement, waveform RAM 26 is loaded with digital data representing the values of the four excitation waveforms to be applied to respective transducers 20a–20d. Each channel has thirty-two 12-bit entries, and each entry represents one point on an excitation waveform. The values of the four channels are interleaved, resulting in a composite table having 128 entries, with consecutive entries being from different channels. Depending upon the values that are stored, the waveforms for the different channels can have different frequencies, different amplitudes, and/or different shapes. Different frequencies are provided by writing more than one cycle of a waveform in the thirty-two entries for a channel. For example, the thirty-two entries might have four cycles (eight entries for each cycle). It is necessary that integer cycles of data be stored in the 32 entries in the table.

Prior to measurement, a calibration procedure is employed for each transducer 20a–20d to determine the coarse calibration factor that will be used to scale the waveform data stored in waveform RAM 26, the imbalance correction added at adder 72, and the fine span correction factor multiplied at multiplier 74. If necessary, the class and units of transducer 20a are determined or verified by measuring the resistance of identification resistor 44. This is done by controlling switch 56 to connect the output of resistance-to-voltage converter 60 to ADC 58, permitting precise measurement of the resistance of identifying resistor 44 using the same high-accuracy components used to process measurements from strain gauge bridge 42. To provide good absolute accuracy, resistance-to-voltage converter 60 is driven from the same DC reference as ADC 58, namely reference 59. This configuration permits discriminating between resistors in 120 ohm increments without cumbersome manual or automatic alignment procedures.

In the calibration procedure, the transducer zero point (i.e., no load being applied at frame 14a) is measured, first with demodulating multiplier 31 receiving data values from demodulation RAM 62 at 0° phase from the input signal (real part), and then with demodulating multiplier receiving data values at 90° phase from the input signal (imaginary part). Shunt resistor 48 is connected to provide the calibration span point, and measurements are taken again at 0° and 90°. The real and imaginary parts of the two measurements are subtracted to obtain a calibration vector. The magnitude of the vector gives the effective change in transducer output with the application of the calibration span point. This value is used to calibrate the amplitude of the excitation waveform stored in waveform RAM 26. The phase of the resultant vector is calculated (arctan imaginary part/real part) and is used as the phase adjustment angle to correct the data stored in demodulation RAM 62.

With the amplitude adjusted and the phase angle corrected by adjusting the data stored in demodulation RAM 62 for the phase angle difference, two more measurements are then taken, one with the span calibration value applied by shunt resistor 46, and one with no load (the "balance" condition). The no-load value is used as an imbalance correction that is added at adder 72, and the ratio of the expected span (span calibration value minus zero) divided by the measured span (the difference in the span calibration value and no-load value) is used to provide a correction factor that is multiplied at multiplier 74. This technique provides quick, efficient and highly accurate calibration, When making measurements, waveform RAM 26 is repetitively addressed to repetitively read out the digital data representing the excitation waveforms. The output of waveform RAM 26 passes through serial interface 30 on board 16 and serial interface 32 on boards 18a–18d.

Referring to FIGS. 3A and 3B, data transmit buffer 92 stores the 12-bit excitation waveform values from waveform RAM 26 (FIG. 2) in interleaved form along with two-bit channel codes and two bits that are not used. As shown in FIG. 3, the stored values for Sample 26 for all four channels are contiguous, and are followed by the values for Sample 27 for all four channels, and so on. The parallel output of buffer 92 is provided to the data transmit shift register 84, which outputs the 16-bit words one bit at a time to buffer 94, which buffers the data provided to the DT line. Register 84 is clocked by 3.36 MHz SCLK pulses generated at divider 82 by dividing the 26.88 MHz frequency output of clock 80 by eight. Frame synchronization generator 86 divides the 3.36 MHz clock from divider 82 by 21 to provide 160 kHz frame synchronization (FS) pulses to sensor conditioning boards 18a–18d. The FS clock is divided in the channel discriminator 88 in each of the sensor conditioning boards 18a–18d by 4 to provide a 40 kHz clock used as a sample clock at ADC 58.

Figure 4A:
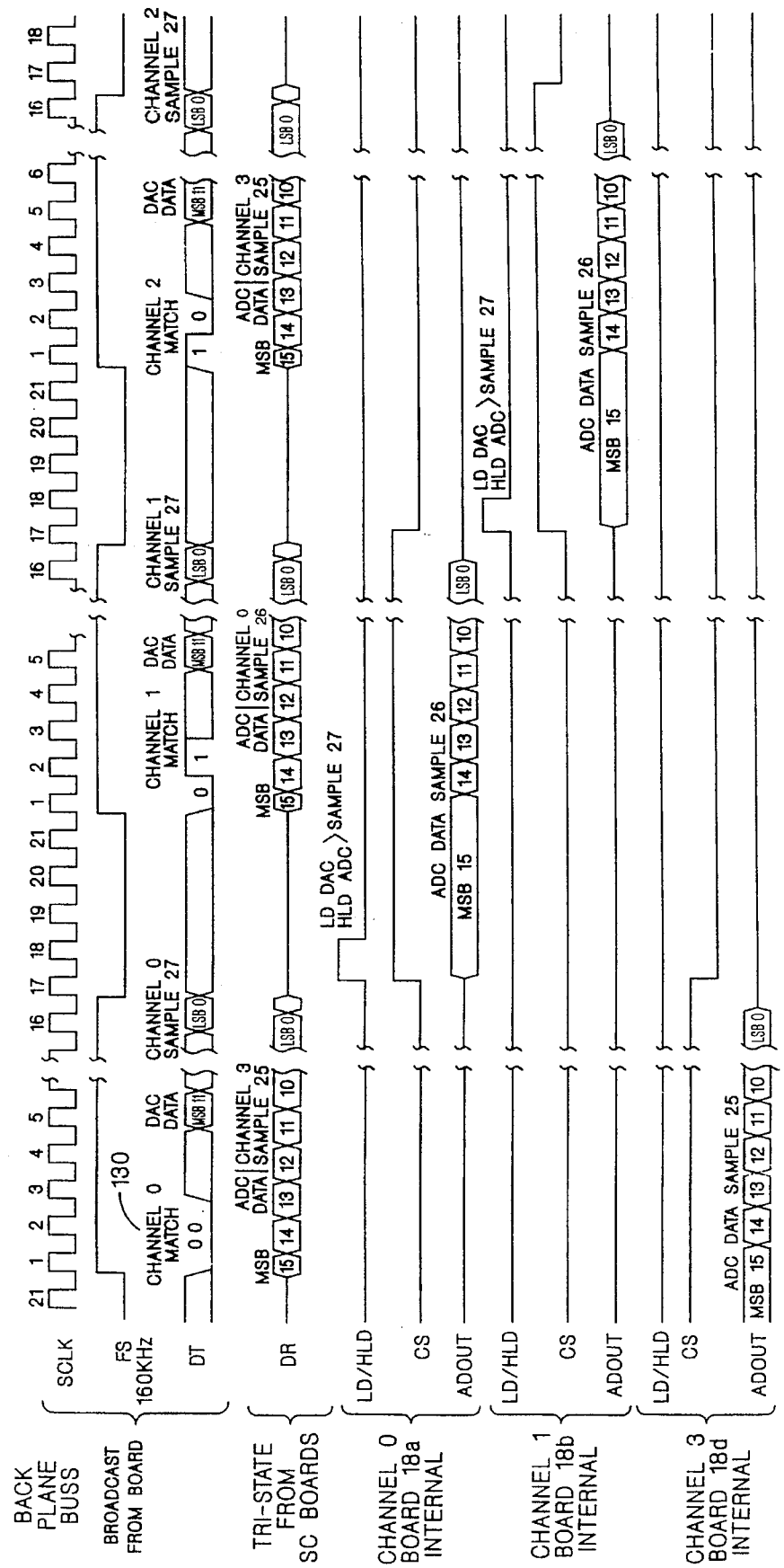
FIGS. 4A and 4B are portions of a timing diagram showing the serial interface operation between a host board and the sensor conditioning boards of the FIG. 1 circuitry.
Figure 4B:
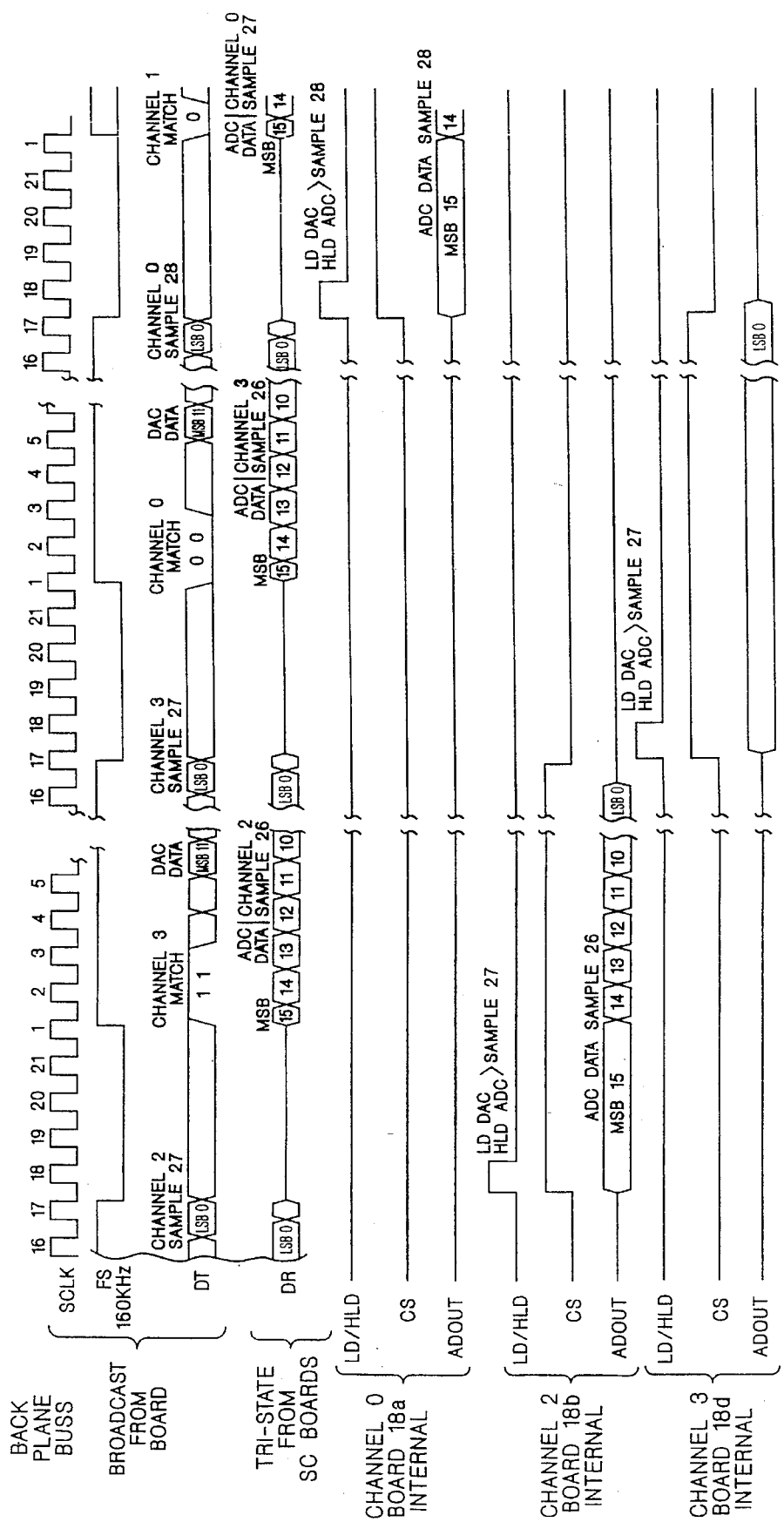

Referring particularly to FIGS. 4A and 4B, the data being sent to or by an individual board 18a–18d are in time slots that are identified by channel code information embedded in the data on the DT line. This provides increased flexibility and improved reliability over the use of dedicated time slots. Each FS cycle is 21 SCLK pulses long, and it takes four FS cycles to transfer four 12-bit DT data words and the associated 2-bit channel codes to respective sensor conditioning boards 18a–18d. (During the same four FS cycles, four 16-bit DR words are sent from the four boards 18a–18d to host board 16.) The 16-bits in data transmit shift register 84 are transmitted during the 21 SCLK pulses in an FS cycle. The 2-bit channel identification code 130 is transmitted during the first and second SCLK pulses, and the 12 bits of the excitation digital data word are transmitted during the fifth through sixteenth SCLK pulses.

On sensor conditioning boards 18a–18d, the excitation waveform data on the DT line are shifted one bit at a time into 16-bit, input shift registers 118 in serial DACs 34 on all sensor conditioning boards 18a–18d, and the 16-bit words stored therein are outputted by registers 118 when clocked by the output of gate 123 subsequent to a falling edge of FS and synchronized to the next SCLK pulse. The bits of the DT data stream are clocked into the state machine in respective channel discriminators 88 on boards 18a–18d by the SCLK pulses, and the embedded channel bits are compared against the encoded channel information (C1, C0) identifying the channel for each board 18a–18d. A mismatch of either bit causes the state machine to enter a standby state. A full match of both bits causes the state machine to generate an LD/HLD pulse that causes the data to be latched into latch 120 and available to the associated parallel input DAC 122, which then changes its analog output based upon the value of the data word. On the other boards 18a–18d, a LD/HLD pulse is not generated for the particular word presently appearing at the output of input register 118; this data word is replaced by the next 16-bit data word shifted into shift register 118, when register 118 is next clocked by the output of gate 123 subsequent to the next falling edge of FS. As shown on FIGS. 4A and 4B, the LD/HLD pulses for the four channels are staggered and coincide with the falling edges of the FS signal after the respective data have been shifted into shift register 118 and before the next data word has begun to be shifted in register 118.

Returning to FIG. 2, the output of DAC 34 is provided to low pass smoothing filter 36, which smooths out the 40 ks/s steps present in the output of DAC 34 and passes a 5 kHz sinusoidal excitation signal with 3% amplitude attenuation. The output of filter 36 is provided to fixed scaling amplifier 38, which provides a gain of 2.6 to guarantee a maximum excitation amplitude of 15 Vrms. The output of fixed scaling amplifier 38 is provided to voltage driver 40, which is capable of driving 15 Vrms into a 120 ohm load. Its balanced output accounts for an effective gain of 2 and allows the excitation voltage levels to be derived from a ±15 volt power supply.

The output of voltage driver 40 is provided over wires 22a to strain gauge resistance bridge 42 of transducer 20a. Transducer 20a modulates the physical variable of interest (load, strain, etc.) with the excitation signal by suppressed carrier amplitude modulation and is mathematically represented as a multiplication.

Instrumentation amplifier 50 receives the balanced, low-level differential output from bridge 42 and outputs an amplified single-ended output signal. The signal dynamics required to perform resolution and differential nonlinearity error (DNL) averaging are injected at the first stage of amplifier 50 in the form of front-end operational amplifier noise of 4 nV/rt(Hz). The consistency of this noise amplitude from system to system is further controlled by Johnson noise as determined by the selective use of gain resistors in the first stage implemented with a 10K/1K/10K resistor network that provides a gain of 21.

Fixed scaling 52 provides a gain of 7.4 to the output of instrumentation amplifier 50 before passing the signal to anti-aliasing filter 54. The 7.4 gain is selected so that serial analog-to-digital converter (ADC) 58 operates at 95% of full signal under conditions of 5 Vrms excitation into a 2 mV/V transducer with allowance of 100% tare. The 5% difference allows for noise, offset, phase error, overrange and other parasitic effects.

Anti-aliasing filter 54 has a cut-off frequency of 20 kHz, which is ½ the 40 ks/s sample rate of ADC 58. The spectrum of interest, 100 Hz, is small compared to the sample rate. This improves noise rejection by minimizing the spectral alias overlap. The output of serial ADC 58 is a 16-bit, 2's complement signal that is passed through serial interfaces 32 and 30.

Referring to FIGS. 3A and 3B, 4A, and 4B, when the LD/HLD signal goes high for one SCLK pulse, parallel output ADC 124 holds the analog signal and converts it to a digital signal, and shift register 126 loads the 16-bit output of the prior sample at ADC 124. At the same time, CS goes high for 21 SCLK pulses (from SCLK pulse 17 of one FS cycle to SCLK, pulse 17 of the next). When the CS and FS signals are both high during SCLK pulses 1 to 16, the 16 SCLK pulses to gate 138 causes gate 138 to output 16 CCLK pulses to shift the 16 bits of the prior sample out of shift register 126. At the same time, the high CS and FS inputs to gate 140 enable buffer 136 to output the 16 bits as the ADOUT signal on the DR line. It is thus seen that the data output on the DR line is skewed by one FS cycle with respect to the data input via the DT line and converted to an analog signal at DAC 34.

The response data on the DR line are buffered at buffer 96 and shifted into 16-bit data receive shift register 98 one bit at a time. Shift register 98 outputs 16-bit words to data receive buffer 100, in which the words are stored in interleaved order for the four channels and ready for access for digital processing on host board 16.

Referring to FIG. 2, the sampled data are demodulated at demodulator 61. Demodulating multiplier 31 multiplies the digital response signal by the excitation waveform values that have been corrected for the difference in phase angle between the excitation waveform provided to sensor conditioning board 18a and the output digital waveform received from board 18a. The phase shifted waveform values are stored in demodulation RAM 62; the waveform values stored in RAM 62 do not have the amplitude adjustment, as do the values stored in RAM 26. This technique is known as suppressed carrier amplitude modulation/synchronous demodulation. The phase correction rejects the quadrature component (which can cause parasitic effects such as sensitivity to cable movement), avoids the loss of headroom resulting from severely phase shifted signals, and, in the case of LVDT's, cancels out temperature sensitivity of the sensed signal. The automatic correction for phase in the calibration and demodulation techniques permits complete interchangeability of conditioner hardware and transducers having differing phase parameters, providing flexibility.

The output of demodulating multiplier 31 is provided to two-stage multirate, low-pass filter 66, which removes the carrier components and improves the resolution and dynamic range by removing frequency components outside the effective signal bandwidth. Because the filtering is implemented by 32-bit floating point arithmetic in the DSP, the precision of 16-bit ADC 58 is extended. The op amp noise density of 4 nV/rt(Hz) and the sample rate of 40,000 s/s (and thus bandwidth of 20,000 Hz) were selected to guarantee sufficient Johnson noise to exercise ADC 58 through 4 codes to permit improved resolution through digital averaging at filter 66.

The demodulated and filtered data from filter 66 are corrected for transducer imbalance errors at adder 72 and for fine span errors at multiplier 74.

The output from multiplier 74 is either used directly, when wide-band data are desired, or passed through variable low-pass filter 76, when narrow band data are desired. Variable low-pass filter 76 can be used to enhance resolution through bandwidth reduction. E.g., bandwidths of 100 Hz (no filtering), 10 Hz, 1 Hz, and 0.1 Hz have estimated resolution (peak to peak noise fluctuation as % of full signal) of 0.005%, 0.0015%, 0.0005%, and 0.00015%. When dynamically applying a load with a servo hydraulic actuator, one would want a wider bandwidth and would sacrifice dynamic range for bandwidth. If one were using a screw drive in a static test, one would probably opt to achieve better resolution at the expense of bandwidth.

The invention has many advantages. Large variations in transducer sensitivity can be easily accommodated by adjustment of excitation amplitude, avoiding the coarse calibration hardware used in classical systems. The amplitude adjustment also permits the normalization of effective noise levels which are required to enhance resolution and dynamic range.

Because DAC 34 and ADC 58 are driven by the same DC reference 59, calibration drift errors due to the DC voltage reference are eliminated. Immediately after calibration, the only absolute error that exists is the accuracy of the calibration reference, which is transducer bridge shunt resistor 46.

ADC resolution and statistically distributed differential nonlinearity errors are minimized by the digital averaging resulting from low pass filtering of a wideband, oversampled signal. Oversampling also reduces the amount of parasitic noise aliasing because the effective signal bandwidth is small compared to the Nyquist rate.

The calibration method and use of digital correction of imbalance and fine span correction avoids the need for coarse balance and zero suppression analog circuitry. Hardware ranging and autoranging circuits are not needed to provide a wide dynamic range; this instead is provided by a high-sample rate ADC. Also, because wideband information is available digitally, via the ADC, high speed event detection and subsequent calculation can be handled in software, eliminating the need for dedicated hardware.

The invention can be easily implemented with most serial interface DAC's and ADC's, and employs reliable state machine technology.

This invention provides flexibility of changing the excitation waveform without requiring additional hardware at the host site, and, in the case of a four-channel system, only requires a single 8-register programmable logic device at each sensor conditioning board.

Other advantages are reduced parts cost, reduced parts count, reduced assembly labor, reduced test complexity, improved reliability, increased functional flexibility and application spectrum, and improved performance.

Other Embodiments

Other embodiments of the invention are within the scope of the following claims.

E.g., the invention can be used with other transducers such as linear variable differential transformers, rotary variable differential transformers, and potentiometric transducers.

What is claimed is:

1. Circuitry for measuring comprising
a random access waveform memory,
means to write a table of excitation digital data representing values of an excitation waveform into said random access waveform memory,
an address generator connected to repetitively address said random access waveform memory to repetitively read out said excitation digital data,
a digital-to-analog converter connected to receive said excitation digital data outputted from said random access waveform memory as its input and to output an analog excitation waveform signal,
a transducer that is electrically connected to receive said analog excitation waveform signal as its input and is physically mounted to react to movement, said transducer providing an analog response signal that is a function of said analog excitation waveform signal and said movement,
an analog-to-digital converter that receives said analog response signal and outputs a digital response signal, and
digital demodulator connected to demodulate said digital response signal based on said excitation digital data.

2. The circuitry of claim 1 wherein said means to write includes means to amplitude adjust source excitation data prior to writing in said random access waveform memory.

3. The circuitry of claim 1 wherein said means to write includes means to write digital data for a plurality of excitation waveforms into said random access waveform memory, and further comprising one or more digital-to-analog converters connected to receive digital data for respective waveforms, and one or more transducers connected to respective said digital-to-analog converters.

4. The circuitry of claim 3 wherein said random access waveform memory contains excitation digital data for waveforms having different frequencies for different transducers.

5. The circuitry of claim 2 wherein said random access waveform memory, said address generator, and said multiplier are implemented by a digital signal processor integrated circuit.

6. The circuitry of claim 1 wherein said random access waveform memory stores data with more than one cycle of said waveform, effectively increasing the frequency of the signal when compared to storing a single cycle of said waveform at the same locations in said random access waveform memory.

7. The circuitry of claim 1 wherein said transducer is a strain gauge.

8. The circuitry of claim 1 wherein said transducer is a linear variable differential transformer, rotary variable differential transformer, or a potentiometric transducer.

9. The circuitry of claim 1 further comprising a correction memory storing a table of correction values based upon said excitation digital data, and wherein said demodulator multiplies said correction values times said digital response signal.

10. The circuitry of claim 9 further comprising a phase shifting means to phase shift said excitation digital data and provide phase shifted data in phase with said digital response signal to said correction memory.

11. The circuitry of claim 10 wherein said phase shifting means calculates a phase shift angle and adjusts the values of said excitation digital data representing values of an excitation waveform to values of said waveform shifted by said angle.

12. The circuitry of claim 1 further comprising a digital low-pass filter that filters said digital response signal, said filter being implemented by a processor having higher resolution than that of said analog-to-digital converter.

13. The circuitry of claim 12 wherein said analog-to-digital converter has a sample rate that is sufficiently high to allow noise bandwidths sufficient to exercise said converter through plural codes.

14. The circuitry of claim 13 further comprising an adder that adds an imbalance correction value to the digital data output by said filter.

15. The circuitry of claim 14 further comprising a span correction multiplier that multiplies a span correction factor times the digital data output by said adder.

16. The circuitry of claim 1 wherein said digital-to-analog converter and said analog-to-digital converter are connected to the same reference voltage source.

17. The circuitry of claim 1 further comprising a phase shifting means to phase shift said excitation digital data and provide phase shifted data in phase with said digital response signal to said demodulator.

18. The circuitry of claim 17 wherein said phase shifting means includes means to calculate a phase shift angle and adjust the values of said excitation digital data of an excitation waveform to values of said waveform shifted by said phase shift angle.

19. The circuitry of claims 18 wherein said phase shifting means is implemented by a digital processor.

20. The circuitry of claim 19 further comprising calibration means to take measurements with different phase angles between the excitation digital data applied to the demodulator and said response signal, and wherein said phase shifting means determines the phase shift angle employing the results of these measurements.

21. The circuitry of claim 20 further comprising an adder that adds an imbalance correction value to the digital data output by said demodulator.

22. The circuitry of claim 21 further comprising a span correction multiplier that multiplies a span correction factor times the digital data output by said adder.

23. The circuitry of claim 17 wherein said digital demodulator comprises a multiplier that multiplies said phase shifted data times the digital response signal and a digital low-pass filter that filters said digital response signal, said filter being implemented by a processor having higher resolution than that of said analog-to-digital converter, said digital low-pass filter removing alternating current components in said digital response signal.

24. The circuitry of claim 12 wherein said analog-to-digital converter has a sample rate that is sufficiently high to allow noise bandwidths sufficient to exercise said converter through plural codes.

25. The circuitry of claim 24 wherein the bandwidth of said analog response signal as presented to said analog-to-digital converter is larger than the bandwidth of said digital low-pass filter.

26. The circuitry of claim 25 further comprising an analog anti-aliasing low-pass filter having a cutoff frequency at ½ the sample rate of said analog-to-digital converter.

27. The circuitry of claim 26 wherein said analog-to-digital converter outputs 16-bit data, and said processor operates on 32-bit floating point data.

28. The circuitry of claim 25 wherein said digital low pass filter has an output with a lower rate than the rate of said analog-to-digital converter.

29. The circuitry of claim 23 wherein said analog-to-digital converter outputs 16-bit data, and said processor operates on 32-bit floating point data.

30. The circuitry of claim 23 wherein said digital low pass filter is a multiple-stage, multirate filter.

31. The circuitry of claim 30 wherein said digital low pass filter has an output with a lower rate than the rate of said analog-to-digital converter.

32. The circuitry of claim 23 further comprising an analog anti-aliasing low-pass filter having a cutoff frequency at ½ the sample rate of said analog-to-digital converter.

33. A method of measuring using excitation waveforms comprising writing excitation digital data into a random access waveform memory, reading digital data from said waveform memory containing a table of excitation digital data to provide a digital excitation waveform signal, converting said digital excitation waveform signal at a digital-to-analog converter to an analog excitation waveform signal, sensing a physical phenomenon with a transducer that receives said analog excitation waveform signal as its input and outputs an analog response signal that is a function of said analog excitation waveform signal and said phenomenon, converting said analog response signal to a digital response signal at an analog-to digital converter, determining a phase angle between said digital response signal and said digital excitation waveform signal, phase shifting said excitation digital data by said phase angle to provide phase-shifted excitation digital data that are in phase with said digital response signal, and demodulating said digital response signal based on said phase-shifted excitation digital data at a digital demodulator to obtain a demodulated digital output.

34. The method of claim 33 wherein said determining a phase angle includes taking measurements with different phase angles between the excitation digital data applied to said demodulator and said response signal.

35. The method of claim 34 wherein said taking measurements includes taking a measurement with the excitation digital data being applied to said demodulator without any phase shifting, and taking a measurement with said excitation digital data being phase shifted 90° before applying to said demodulator.

36. The method of claim 35 wherein said taking measurements includes taking measurements at different phenomenon conditions without any phase shifting of said excitation digital data applied to said demodulator to obtain a real part and with 90° phase shifting of said excitation digital data applied to said demodulator to obtain an imaginary part, and wherein said determining includes taking the difference between the imaginary parts and real parts to obtain a calibration vector, the angle of which is taken as said phase angle between said digital response signal and said digital excitation waveform signal.

37. The method of claim 36 wherein further comprising amplitude adjusting said excitation digital data prior to said converting by an amount related to the magnitude of said calibration vector.

38. The method of claim 37 further comprising taking measurements at different known phenomenon conditions with said excitation digital data being phase shifted by said phase angle before applying to said demodulator, and calculating an imbalance correction value based upon the difference between the expected and the measured lower phenomenon condition and calculating a span correction value based upon the ratio of the measured difference between values and the expected difference, and further comprising adding said imbalance correction value to said demodulated digital output to obtain an imbalance-corrected digital output and multiplying said span correction value times said imbalance-corrected digital output.

39. The method of claim 33 wherein said transducer is physically mounted to react to the strain of a component in a load string of a material testing instrument.

40. The method of claim 36 wherein said transducer is physically mounted to react to the strain of a component in a load string of a material testing instrument.

41. The method of claim 38 wherein said transducer is physically mounted to react to the strain of a component in a load string of a material testing instrument.

* * * * *